United States Patent [19]

Timmler et al.

[11] 4,127,404

[45] Nov. 28, 1978

[54] 4-AMINO-1,2,4-TRIAZIN-5-ONE COMPOUNDS AND HERBICIDAL COMPOSITIONS

[75] Inventors: Helmut Timmler; Wilfried Draber, both of Wuppertal; Ludwig Eue, Leverkusen, all of Germany

[73] Assignee: Bayer Aktiengesellschaft, Leverkusen, Germany

[21] Appl. No.: 837,340

[22] Filed: Sep. 28, 1977

[30] Foreign Application Priority Data

Oct. 21, 1976 [DE] Fed. Rep. of Germany ....... 2647460

[51] Int. Cl.$^2$ ................... C07D 253/06; A01N 9/12; A01N 9/22
[52] U.S. Cl. ........................................ 71/90; 544/182; 71/93
[58] Field of Search ....................... 544/182; 71/93, 90

[56] References Cited

FOREIGN PATENT DOCUMENTS 233,561  5/1964  Austria ..................................... 544/182

*Primary Examiner*—John M. Ford
*Attorney, Agent, or Firm*—Sprung, Felfe, Horn, Lynch & Kramer

[57] ABSTRACT

New heterocyclically-substituted 4-amino-1,2,4-triazin-5-one compounds, herbicidal compositions containing them and their use as herbicides are disclosed.

It is known that 1,2,4-triazionones, such as, for example, 4-amino-3-methyl-6-phenyl-1,2,4-triazine-5-one, can be used for combatting weeds, especially for selectively combatting weeds, from German Offenlegungsschrift (German Published Specification) 2,224,161. Their general herbicidal action is, however, not always entirely statisfactory, especially when low amounts and low concentrations are used.

37 Claims, No Drawings

4-AMINO-1,2,4-TRIAZIN-5-ONE COMPOUNDS AND HERBICIDAL COMPOSITIONS

The present invention now provides, as new compounds, the heterocyclically-substituted 4-amino-1,2,4-triazin-5-one of the general formula

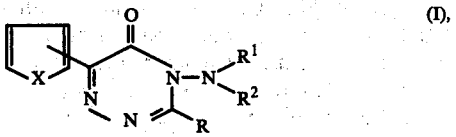

in which
R is hydrogen, alkyl, alkenyl, cycloalkyl, optionally substituted phenyl or optionally substituted phenylalkyl,
$R^1$ is hydrogen or alkyl,
$R^2$ is hydrogen, alkyl, halogenoalkyl, optionally substituted phenyl or optionally substituted phenylalkyl and
X is oxygen, sulfur or the NH group, and their salts exhibit outstanding herbicidal properties and are useful particularly as selective herbicides.

The present invention relates to certain new heterocyclically-substituted 4-amino-1,2,4-triazin-5-one compounds, to herbicidal compositions containing them and to their use as herbicides.

It is known that 1,2,4-triazionones, such as, for example, 4-amino-3-methyl-6-phenyl-1,2,4-triazine-5-one, can be used for combatting weeds, especially for selectively combatting weeds, from German Offenlegungsschrift (German Published Specification) 2,224,161. Their general herbicidal action is, however, not always entirely statisfactory, especially when low amounts and low concentrations are used.

The present invention now provides, as new compounds, the heterocyclically-substituted 4-amino-1,2,4-triazin-5-one of the general formula

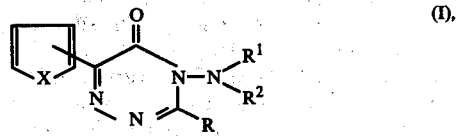

in which
R is hydrogen, alkyl, alkenyl, cycloalkyl, optionally substituted phenyl or optionally substituted phenylalkyl,
$R^1$ is hydrogen or alkyl,
$R^2$ is hydrogen, alkyl, halogenoalkyl, optionally substituted phenyl or optionally substituted phenylalkyl and
X is oxygen, sulfur or the NH group, and their salts.

The compounds of the invention exhibit very good herbicidal properties.

Preferably, R represents hydrogen, straight-chain or branched alkyl with 1 to 6 (especially with 1 to 4) carbon atoms, straight-chain or branched alkenyl with 2 to 6 carbon atoms, cycloalkyl with 3 to 6 carbon atoms, phenyl or phenylalkyl with 1 or 2 carbon atoms in the alkyl part, the benzene ring of the last two radicals optionally being substituted by halogen (especially fluorine, chlorine or bromine), hydroxyl, alkyl with 1 to 4 carbon atoms, alkoxy with 1 to 4 carbon atoms or halogenoalkyl with 2 to 5 halogen atoms (especially fluorine or chlorine) and 1 to 2 carbon atoms (such as, for example, trifluoromethyl), $R^1$ represents hydrogen or straight-chain or branched alkyl with 1 to 6 (especially with 1 to 4) carbon atoms, and $R^2$ represents hydrogen, straight-chain or branched alkyl with 1 to 6 (especially with 1 to 4) carbon atoms, halogenoalkyl with 1 to 4 carbon atoms and 1 to 5 (especially 1 to 3) halogen atoms (preferred halogens being fluorine and chlorine, and trifluoromethyl being an example of such halogenoalkyl), phenyl or phenylalkyl with 1 or 2 carbon atoms in the alkyl part, the benzene rings of the last two radicals being optionally substituted by halogen (especially fluorine, chlorine or bromine), alkyl with 1 to 4 carbon atoms, alkoxy with 1 to 4 carbon atoms or alkylthio with 1 to 4 carbon atoms.

The five-membered heterocyclic ring is bonded to the 1,2,4-triazin-5-one in the 2- or 3-position.

The invention also provides a process for the preparation of a heterocyclically-substituted 4-amino-1,2,4-triazin-5-one of the formula (I) in which a diazabutadiene of the general formula

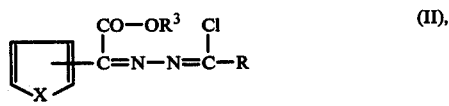

in which
R and X have the above-mentioned meanings and
$R^3$ represents alkyl, preferably with 1 to 4 carbon atoms, is reacted with a hydrazine derivative of the general formula

in which $R^1$ and $R^2$ have the above-mentioned meanings, if appropriate in the presence of a diluent and, if appropriate, in the presence of an acid-binding agent, and then if required, the base (I) is converted into a salt thereof by reaction with an acid.

In some cases it provies advantageous to prepare the compounds according to the invention, in which $R^1$ and $R^2$ represent hydrogen, by other generally customary routes, for example by (a) reacting the corresponding glyoxylic acid alkyl ester 2-acylhydrazones with hydrazine hydrate in the presence of polar organic solvents at temperatures between 0° and 50° C., isolating the glyoxylic acid hydrazide 2-acylhydrazones hereupon formed and then heating them in the presence of a polar organic solvent and, if appropriate, of a water-binding agent, to temperatures between 60° and 150° C. see German Offenlegungsschrift (German Published Specification) 2,364,474 or (b) reacting the corresponding glyoxylic acid alkyl esters with corresponding hydrazidines (see Liebigs Ann.Chem. 1975, 1120-1123), if appropriate in the presence of a polar solvent, at temperatures between 40° and 120° C.

Surprisingly, the heterocyclically-substituted 4-amino-1,2,4-triazin-5-ones according to the invention, of the formula (I), exhibit a better herbicidal action than the active compound 4-amino-3-methyl-6-phenyl-1,2,4-triazin-5-one, known from the state of the art, which action is particularly pronounced against Echinochloa crus-galli. The active compounds according to the invention thus represent an enrichment of the art.

If 1-ethoxycarbonyl-4-chloro-4-methyl-1-thien-2-yl-2,3-diazabutadiene and hydrazine are used as starting materials, the course of the reaction can be represented by the following equation:

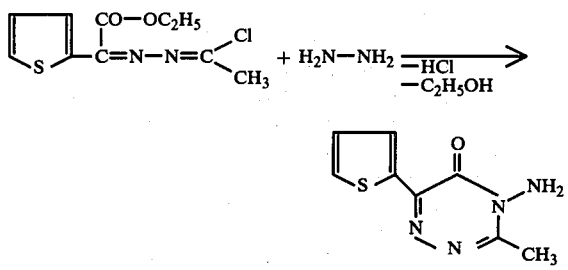

The following may be mentioned individually as examples of the diazabutadienes of the formula (II) to be used, according to the invention, as starting materials: 1-ethoxycarbonyl-1-thien-2-yl-4-chloro-4-methyl-2,3-diazabutadiene, 1-ethoxy-carbonyl-1-thien-3-yl-4-chloro-4-methyl-2,3-diazabutadiene, 1-ethoxycarbonyl-1-fur-2-yl-4-chloro-4-methyl-2,3-diazabutadiene, 1-ethoxycarbonyl-1-fur-3-yl-4-chloro-4-methyl-2,3-diazabutadiene, 1-ethoxycarbonyl-1-pyrrol-2-yl-4-chloro-4-methyl-2,3-diazabutadiene, 1-ethoxycarbonyl-1-pyrrol-3-yl-4-chloro-4-methyl-2,3-diazabutadiene, 1-ethoxycarbonyl-1-thien-2-yl-4-chloro-4-ethyl-2,3-diazabutadiene, 1-ethoxycarbonyl-1-thiene-2-yl-4-chloro-4-n-propyl-2,3-diazabutadiene, 1-ethoxycarbonyl-1-thien-2-yl-4-chloro-4-iso-propyl-2,3-diazabutadiene, 1-ethoxycarbonyl-1-thien-2-yl-4-chloro-4-n-butyl-2,3-diazabutadiene, 1-ethoxycarbonyl-1-thien-2-yl-4-chloro-4-sec.butyl-2,3-diazabutadiene, 1-ethoxycarbonyl-1-thien-2-yl-4-chloro-4-tert.-butyl-2,3-diazabutadiene, 1-ethoxycarbonyl-1-thien-2-yl-4-chloro-4-cyclopropyl-2,3-diazabutadiene, 1-ethoxycarbonyl-1-thien-2-yl-4-chloro-4-cyclopentyl-2,3-diazabutadiene, 1-ethoxycarbonyl-1-thien-2-yl-4-chloro-4-cyclohexyl-2,3-diazabutadiene, 1-ethoxycarbonyl-1-thien-2-yl-4-chloro-4-phenyl-2,3-diazabutadiene, 1-ethoxycarbonyl-1-thien-2-yl-4-chloro-4-benzyl-2,3-diazabutadiene, 1-ethoxycarbonyl-1-thien-2-yl-4-chloro-4-allyl-2,3-diazabutadiene, 1-ethoxycarbonyl-1-fur-2-yl-4-chloro-4-ethyl-2,3-diazabutadiene, 1-ethoxycarbonyl-1-fur-2-yl-4-chloro-4-n-propyl-2,3-diazabutadiene, 1-ethoxycarbonyl-1-fur-2-yl-4-chloro-4-iso-propyl-2,3-diazabutadiene, 1-ethoxycarbonyl-1-fur-2-yl-4-chloro-4-n-butyl-2,3-diazabutadiene, 1-ethoxycarbonyl-1-fur-2-yl-4-chloro-4-sec.-butyl-2,3-diazabutadiene, 1-ethoxycarbonyl-1-fur-2-yl-4-chloro-4-tert.-butyl-2,3-diazabutadiene, 1-ethoxycarbonyl-1-fur-2-yl-4-chloro-4-cyclopropyl-2,3-diazabutadiene, 1-ethoxycarbonyl-1-fur-2-yl-4-chloro-4-cyclopentyl-2,3-diazabutadiene, 1-ethoxycarbonyl-1-fur-2-yl-4-chloro-4-cyclohexyl-2,3-diazabutadiene, 1-ethoxycarbonyl-1-fur-2-yl-4-chloro-4-phenyl-2,3-diazabutadiene, 1-ethoxycarbonyl-1-fur-2-yl-4-chloro-4-benzyl-2,3-diazabutadiene and 1-ethoxycarbonyl-1-fur-2-yl-4-chloro-4-allyl-2,3-diazabutadiene.

The diazabutadienes of the formula (II) used as starting materials have not previously been disclosed in the literature. However, they are obtained by a generally known method (see German Offenlegungsschrift (German Published Specification) 2,138,031) by reacting glyoxylic acid ester 2-acylhydrazones of the general formula

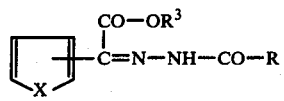

in which R, $R^3$ and X have the above-mentioned meanings, with chlorinating agents, such as phosphorus pentachloride or phosphorus pentabromide, thionyl chloride or phosgene, at temperatures between $-10°$ and $100°$ C., if appropriate in the presence of a diluent, for example methylene chloride or chloroform (see the preparative Examples given later in this text).

Glyoxylic acid ester 2-acylhydrazones of the formula (IV) have not previously been described in the literature. However, they can be prepared in known manner (see German Offenlegungsschriften (German Published Specifications) 2,107,757 and 2,364,474) by reacting known glyoxylic acid esters of the general formula

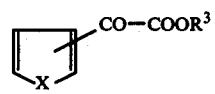

in which
$R^3$ and X have the above-mentioned meanings, with an acylhydrazine of the general formula $$H_2N - NH - CO - R \qquad (VI),$$

in which
R has the above-mentioned meaning, in the presence of a diluent, for example on alcohol, such as methanol or ethanol, and, if appropriate, in the presence of an acid catalyst, at temperatures between 50° and 130° C. (see the preparative Examples).

The hydrazine derivatives of the formula (III) to be used as starting materials are generally known compounds.

Suitable salts of the compounds according to the invention of the formula (I) are salts with physiologically tolerated acids. Amongst these, the hydrogen halide acids (such as, for example, hydrobromic acid and especially hydrochloric acid), phosphoric acid, nitric acid, monofunctional and bifunctional carboxylic acids and hydroxycarboxylic acids (such as, for example, acetic acid, maleic acid, succinic acid, fumaric acid, citric acid, salicylic acid, sorbic acid, tartaric acid and lactic acid) and 1,5-naphthalene-disulphonic acid, are preferred.

The salts of the compounds of the formula (1) can be obtained in a simple manner in accordance with customary methods of forming salts, for example by dissolving the base in an ether, for example diethyl ether, and adding the acid, for example nitric acid, and can be isolated in a known manner, for example by filtering off, and be purified if appropriate.

Suitable diluents for the reaction according to the invention are all polar orgaic solvents. Amongst these, alcohols such as methanol, ethanol and isopropanol, ethers, such as tetrahydrofuran or dioxan, nitriles, such as tolunitrile or acetonitrile, acid amides, such as dimethylformamide, and sulphoxides, such as dimethylsulphoxide, are preferred.

The reaction according to the invention is usually carried out in the presence of an acid-binding agent. Amongst these, alkali metal carbonates, such as, for example, sodium carbonate, potassium carbonate and sodium bicarbonate, alkaline earth metal carbonates, such as, for example, barium carbonate, lower tertiary alkylamines, such as, for example, triethylamine, and also pyridine, are preferred. Preferably, an excess of the hydrazine derivative of the formula (III) is used as the acid-binding agent.

The reaction temperatures can be varied within a fairly wide range. In general, the reaction is carried out at from 20° to 120° C., preferably from 50° to 100° C.

In carrying out the process according to the invention, 1 mole of hydrazine of the formula (III) and 1 mole of acid-binding agent are generally employed per mole of diazabutadiene of the formula (II). Preferably, an excess of hydrazine is employed as the acid-binding agent, in general 2 to 5 moles. However, using greater or lesser amounts than these produces no significant improvement in yield.

The compounds of the formula (I) may be isolated in the generally customary manner.

In addition to the compounds of the preparative Examples the following may be mentioned as particularly active compounds: 3-cyclopropyl-4-amino-6-thien-2-yl-1,2,4-triazin-5-one, 3-n-butyl-4-amino-6-thien-2-yl-1,2,4-triazin-5-one, 3-sec.-butyl-4-amino-6-thien-2-yl-1,2,4-triazin-5-one, 3-tert.-butyl-4-amino-6-thien-2-yl-1,2,4-triazin-5-one, 3-n-propyl-4-amino-6-thien-2-yl-1,2,4-triazin-5-one, 3-cyclopentyl-4-amino-6-thien-2-yl-1,2,4-triazin-5-one, 3-cyclohexyl-4-amino-6-thien-2-yl-1,2,4-triazin-5-one, 3-phenyl-4-amino-6-thien-2-yl-1,2,4-triazin-5-one, 3-benzyl-4-amino-6-thien-2-yl-1,2,4-triazin-5-one, 3-cyclopropyl-4-methylamino-6-thien-2-yl-1,2,4-triazin-5-one, 3-n-butyl-4-methylamino-6-thien-2-yl-1,2,4-triazin-5-one, 3-sec.-butyl-4-methylamino-6-thien-2-yl-1,2,4-triazin-5-one, 3-tert.-butyl-4-methylamino-6-thien-2-yl-1,2,4-triazin-5-one, 3-n-propyl-4-methylamino-6-thien-2-yl-1,2,4-triazin-5-one, 3-cyclopentyl-4-methylamino-6-thien-2-yl-1,2,4-triazin-5-one, 3-cyclohexyl-4-methylamino-6-thien-2-yl-1,2,4-triazin-5-one, 3-phenyl-4-methylamino-6-thien-2-yl-1,2,4-triazin-5-one, 3-benzyl-4-methylamino-6-thien-2-yl-1,2,4-triazin-5-one, 3-ethyl-4-amino-6-fur-2-yl-1,2,4-triazin-5-one, 3-iso-propyl-4-amino-6-fur-2-yl-1,2,4-triazin-5-one, 3-cyclopropyl-4-amino-6-fur-2-yl-1,2,4-triazin-5-one, 3-tert.-butyl-4-amino-6-fur-2-yl-1,2,4-triazin-5-one, 3-n-propyl-4-amino-6-fur-2-yl-1,2,4-triazin-5-one, 3-cyclopentyl-4-amino-6-fur-2-yl-1,2,4-triazin-5-one, 3-cyclohexyl-4-amino-6-fur-2-yl-1,2,4-triazin-5-one, 3-phenyl-4-amino-6-fur-2-yl-1,2,4-triazin-5-one, 3-benzyl-4-amino-6-fur-2-yl-1,2,4-triazin-5-one, 3-ethyl-4-methylamino-6-fur-2-yl-1,2,4-triazin-5-one, 3-iso-propyl-4-methylamino-6-fur-2-yl-1,2,4-triazin-5-one, 3-cyclopropyl-4-methylamino-6-fur-2-yl-1,2,4-triazin-5-one, 3-tert.-butyl-4-methylamino-6-fur-2-yl-1,2,4-triazin-5-one, 3-n-propyl-4-methylamino-6-fur-2-yl-1,2,4-triazin-5-one, 3-cyclopentyl-4-methylamino-6-fur-2-yl-1,2,4-triazin-5-one, 3-cyclohexyl-4-methylamino-6-fur-2-yl-1,2,4-triazin-5-one, 3-phenyl-4-methylamino-6-fur-2-yl-1,2,4-triazin-5-one, 3-benzyl-4-methylamino-6-fur-2-yl-1,2,4-triazin-5-one, 3-methyl-4-amino-6-pyrrol-2-yl-1,2,4-triazin-5-one, 3-ethyl-4-amino-6-pyrrol-2-yl-1,2,4-triazin-5-one, 3-methyl-4-methylamino-6-pyrrol-2-yl-1,2,4-triazin-5-one and 3-ethyl-4-methylamino-6-pyrrol-2-yl-1,2,4-triazin-5-one.

The active compounds according to the invention influence plant growth and can therefore be used as defoliants, desiccants, agents for destroying broad-leaved plants, germination inhibitors and, especially, weedkillers. Whether the compounds according to the invention act as total or selective herbicides depends essentially on the amount used.

By "weeds" in the broadest sense there are meant plants growing in locations where they are not desired.

The active compounds according to the present invention may be used, for example, to combat the following plants:

dicotyledon weeds such as mustard (*Sinapis*), cress (*Lepidium*), bed straw (*Galium*), chickweed (*Stellaria*), camomile (*Matricaria*), mayweed (*Anthemis*), gallant soldier (*Galinsoga*), goosefoot (*Chenopodium*), annual nettle (*Urtica*), groundsel (*Senecio*), pigweed (*Amaranthus*), purslane (*Portulaca*), cocklebur (*Xanthium*), bindweed (*Convolvulus*), morning glory (*Ipomoea*), knotweed (*Polygonum*), sesbania (*Sesbania*), ragweed (*Ambrosia*), spear thistle (*Cirsium*), common thistle (*Carduus*), sow thistle (*Sonchus*), field cress (*Rorippa*), toothcup (*Rotala*), false pimpernel (*Linderna*), deadnettle (*Lamium*), speedwell (*Veronica*), mallow (*Abutilon*), emex (*Emex*), thornapple (Datura), violet (*Viola*), hemp-nettle (*Galeopsis*), poppy (*Papaver*) and knapweed (*Centaurea*); and monocotyledon weeds such as barnyard grass (*Echinochloa*), foxtail (*Setaria*), wild millet (*Panicum*), crabgrass (*Digitaria*), timothy (*Phleum*), bluegrass (*Poa*), fescue (*Festuca*), goosegrass (*Eleusine*), signalgrass (*Brachiaria*), ryegrass (*Lolium*), cheat (*Bromus*), oats (*Avena*), flatsedge (*Cyperus*), sorghum (*Sorghum*), quackgrass (*Agropyron*), Bermuda grass (*Cynodon*), *Monocharia,* fimbristylis (*Fimbristylis*), arrowhead (*Sagittaria*), spikerush (*Eleocharis*), bulrush (*Scirpus*), paspalum (*Paspalum*), Ischaemum, gooseweed (*Sphenoclea*), crowfoot grass (Dactyloctenium), redtop (*Agrostis*), meadow foxtail (*Alopecurus*) and silky bent-grass (*Apera*).

The active compounds according to the present invention may be used, for example, as selective herbicides in the following cultures:

dicotyledon cultures such as cotton (*Gossypium*), soya bean (*Glycine*), beet (*Beta*), carrot (*Daucus*), bean (*Phaseolus*), pea (*Pisum*), potato (*Solanum*), flax (*Linum*), sweet potato (*Ipomoea*), broad bean (*Vicia*) tobacco (*Nicotiana*), tomato (*Lycopersicon*), groundnut (*Arachis*), cabbage (*Brassica*), lettuce (*Lactuca*), cucumber (*Cucumis*) and marrow (*Cucurbita*); and monocotyledon cultures such as rice (*Oryza*), maize (*Zea*), wheat (*Triticum*), barley (*Hordeum*), oats (*Avena*), rye (*Secale*), sorghum (*Sorghum*), millet (*Panicum*), sugar cane (*Saccharum*), pineapple (*Ananas*), asparagus (*Asparagus*) and onion (*Allium*).

However, the use of the active compounds according to the invention is in no way restricted to these plants or even to the indicated genera but also embraces other plants, in the same way.

Depending on the concentration, the compounds can be used for the total combating of weeds, for example on industrial terrain and railway tracks and on paths and squares with and without trees. Equally, the compounds can be employed for combating weeds in perennial cultures, for example forestry plantings, decorative tree plantings, orchards, vineyards, citrus groves, nut orchards, banana plantations, coffee planatations, tea plantations, rubber plantations, oil palm plantations, soft fruit plantings and hopfields, and for the selective combating of weeds in annual cultures.

The active compounds according to the invention can be converted into the usual formulations, such as solutions, emulsions, suspensions, powders, pastes and granules.

These formulations may be produced in known manner, for example by mixing the active compounds with extenders, that is to say, liquid or solid or liquefied gaseous diluents or carriers, optionally with the use of surfaceactive agents, that is to say, emulsifying agents and/or dispersing agents and/or forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene, benzene or alkyl-naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as dichlorodifluoromethane or trichlorofluoromethane.

As solid carriers there are preferably used ground natural minerals, such as kaolins, clays, talc, chalk, quartz, attapulgite, montmorillonite or diatomaceous earth, and ground synthetic minerals, such as highly dispersed silicic acid, alumina and silicates.

Preferred examples of emulsifying and foam-forming agents include nonionic and anionic emulsifiers, such as polyoxyethylene-fatty acid esters, polyoxyethylenefatty alcohol ethers, for example alkylaryl polyglycol ethers, alkyl sulphonates, alkyl sulphates and aryl sulphonates as well as albumin hydrolysis products; and preferred examples of dispersing agents include lignin sulphite waste liquors and methylcellulose.

The active compounds according to the invention, as such or in their formulations, can be combined with other herbicidal active compounds to boost and supplement their spectrum of action, depending on the intended use; for this purpose, finished formulations or tank mixing may be employed.

The active compounds according to the invention can be present in the formulations as mixtures with other active compounds, such as fungicides, insecticides and acaricides.

The formulations in general contain from 0.1 to 95 per cent by weight of active compound, preferably from 0.5 to 90 per cent by weight.

The active compounds can be used as such, as their formulations or as the use forms prepared therefrom, such as ready-to-use solutions, emulsions, suspensions, powders, pastes and granules. They may be used in the customary manner, for example by spraying, atomising, dusting, scattering and watering.

The amount of active compound used can vary within a fairly wide range. It depends essentially on the nature of the desired effect. In general, the amounts used are from 0.1 to 20 kg of active compound per hectare, preferably from 0.2 to 15 kg/ha.

The active compounds according to the invention are particularly suitable for the selective combating of weeds in cereals and cotton.

The active compounds can be used both in accordance with the post-emergence method and in accordance with the pre-emergence method.

The present compounds in some cases also possess bactericidal and fungicidal activity, for example against diseases of cereals.

The present invention also provides a herbicidal composition containing as active ingredient a compound of the present invention in admixture with a solid or liquefied gaseous diluent or carrier or in admixture with a liquid diluent or carrier containing a surfaceactive agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides means of yielding crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

(A) = [structure: phenyl-C(=O)-C(=N-N=)-N-NH$_2$ with N-CH$_3$]

EXAMPLE A

Post-emergence Test
Solvent: 5 parts by weight of acetone
Emulsifier: 1 part by weight of alkylaryl polyglycol ether To produce a suitable preparation of active compound 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which are indicated in the table. The concentration of the spray liquor was so chosen that the amounts of active compound shown in the table were applied in 2,000 l of water/ha. After three weeks, the degree of damage to the plants was rated in % damage in comparison to the development of the untreated control. The figures denoted:

0% = no action (like untreated control)
100% = total destruction.

The active compounds, the amounts applied and the results can be seen from the table which follows:

TABLE A

| Active compound | Amount of active compound used kg/ha | Post-emergence Test | | | | | | | |
|---|---|---|---|---|---|---|---|---|---|
| | | Echino-chloa | Sina-pis | Galin-soga | Stella-ria | Urtica | Daucus | Cotton | Wheat |
| (A) | 1 | 40 | 80 | 100 | 100 | 100 | 100 | 0 | 40 |
| (1) | 1 | 90 | 100 | 100 | 100 | 100 | 80 | 0 | 0 |
| (2) | 1 | 100 | 100 | 100 | 100 | 100 | 100 | 60 | 0 |
| (3) | 1 | 100 | 100 | 100 | 100 | 100 | 100 | 40 | 60 |
| (4) | 1 | 100 | 100 | 100 | 100 | 100 | 100 | 80 | 50 |
| (5) | 1 | 80 | 100 | 100 | 100 | 100 | 100 | 0 | 60 |

The process of the present invention is illustrated by the following preparative Examples.

EXAMPLE 1

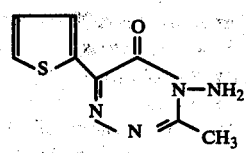
(1)

234 g (0.92 mol) of crude 1-ethoxycarbonyl-4-chloro-4-methyl-1-thien-2-yl-2,3-diazabutadiene were dissolved in 600 ml of isopropanol and 125 g (2.5 mol) of hydrazine hydrate were added at 60° C., whilst stirring. Stirring was continued for 8 hours at 60° C. The reaction solution was concentrated to one-third and water was added. The solid which had precipitated was then filtered off, thoroughly rinsed with water and dried. 125g (65.3% of theory) of 4-amino-3-methyl-6-thien-2-yl-1,2,4-triazin-5-one of melting point 210° C. were obtained.

Preparation of the starting material

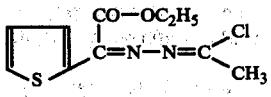
(1-a)

240 g (1 mol) of thien-2-yl-glyoxylic acid ethyl ester 2-acetylhydrazone were dissolved in 1,000 ml of methylene chloride and 208 g (1 mol) of phosphorus pentachloride were added at −10° to 0° C. Stirring was continued for half an hour, ice-water was added to the reaction mixture and the batch was neutralised with sodium bicarbonate solution. The organic phase was separated off, dried over sodium sulphate and concentrated by distilling off the solvent. 234 g (0.92 mol) of crude 1-ethoxycarbonyl-4-chloro-4-methyl-1-thien-2-yl-2,3-diazabutadiene were obtained as an oil which would be directly reacted further.

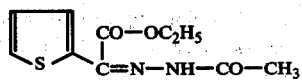
(1-b)

184 g (1 mol) of thien-2-yl-glyoxylic acid ethyl ester [see Beilsteins Handbuch der Organ. Chemie (Beilsteins Handbook of Organic Chemistry), Volume 18, page 407 and E II, page 326] were dissolved in 500 ml of ethanol and 74 g (1 mol) of acetylhydrazine were added. The mixture was heated under reflux for 8 hours. After distilling off the solvent, 200 g (83.3% of theory) of thien-2-yl-glyoxylic acid ethyl ester 2-acetylhydrazone of melting point 76° C. were obtained.

The compounds of Table 1 below were obtained by methods analogous to that of Example 1.

Table 1

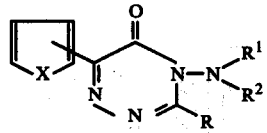

| Ex. No. | R | $R^1$ | $R^2$ | X | Position where the heterocyclic ring is linked | Melting point (° C) |
|---|---|---|---|---|---|---|
| 2 | $CH_3$ | H | $CH_3$ | S | 2 | 154 |
| 3 | $C_2H_5$ | H | H | S | 2 | 208 |
| 4 | $C_2H_5$ | H | $CH_3$ | S | 2 | 111 |
| 5 | $C_2H_5$ | H | H | S | 2 | 235 (decomposition) (xHCl) |
| 6 | i-$C_3H_7$ | H | $CH_3$ | S | 2 | 210 (decomposition) (xHCl) |
| 7 | i-$C_3H_7$ | H | H | S | 2 | 177 |
| 8 | $CH_3$ | H | H | O | 2 | 247 |
| 9 | $CH_3$ | H | H | O | 3 | 180 |
| 10 | t-$C_4H_9$ | H | H | S | 2 | 189 |

It will be understood that the specification and examples are illustrative but not limitative of the present invention and that other embodiments within the spirit and scope of the invention will suggest themselves to those skilled in the art.

What is claimed is:

1. 4-Amino-1,2,4-triazin-5-one compound of the formula (I), wherein

R is hydrogen, alkyl of up to 6 carbon atoms, alkenyl of up to 6 carbon atoms, cycloalkyl of from 3 to 6 carbon atoms, phenyl, phenylalkyl, wherein the alkyl moiety has up to 2 carbon atoms, substituted phenyl, and substituted phenylalkyl wherein the benzene moiety is substituted with at least one of halogen, hydroxyl alkyl of up to 4 carbon atoms, alkoxy of up to 4 carbon atoms, or haloalkyl of up to 2 carbon atoms and up to 5 halo atoms, $R^1$ is halogen or alkyl of up to 6 carbon atoms, $R^2$ is hydrogen, alkyl of up to 6 carbon atoms, haloalkyl of up to 4 carbon atoms and up to 5 halo atoms, phenyl, phenylalkyl of up to 2 carbon atoms in the alkyl moiety, substituted phenyl, and substituted phenylalkyl wherein the benzene ring is substituted with at least one of halogen alkyl of up to 4 carbon atoms, alkoxy of up to carbon atoms or alkylthio of up to 4 carbon atoms, and X is oxygen, sulfur or the NH group and salts thereof.

2. Compound as claimed in claim 1 wherein R is hydrogen.

3. Compound as claimed in claim 1 wherein R is alkyl or alkenyl of up to 6 carbon atoms.

4. Compound as claimed in claim 1 wherein R is cycloalkyl of 3 to 6 ring carbon atoms.

5. Compound as claimed in claim 1 wherein R is phenyl or phenylalkyl of 1 to 2 carbon atoms in the alkyl moiety and wherein the benzene ring may be substituted by halogen, hydroxyl, alkyl or alkoxy of up to 4 carbon atoms, or haloalkyl of 1 to 2 carbon atoms and 2 to 5 halogen atoms.

6. Compound as claimed in claim 1 wherein $R^1$ is hydrogen.

7. Compound as claimed in claim 1 wherein $R^1$ is alkyl of up to 6 carbon atoms.

8. Compound as claimed in claim 1 wherein $R^2$ is hydrogen.

9. Compound as claimed in claim 1 wherein $R^2$ is alkyl or haloalkyl of up to 4 carbon atoms.

10. Compound as claimed in claim 1 wherein $R^2$ is phenyl or phenylalkyl of 1 to 2 carbon atoms in the alkyl moiety wherein the benzene ring may be substituted by halogen or alkyl, alkoxy or alkylthio of up to 4 carbon atoms.

11. Compound as claimed in claim 1 wherein X is oxygen.

12. Compound as claimed in claim 1 wherein X is sulfur.

13. Compound as claimed in claim 1 wherein X is the NH group.

14. Compound as claimed in claim 1 designated 4-amino-3-methyl-6-thien-2-yl-1,2,4-triazin-5-one.

15. Compound as claimed in claim 1 designated 4-methylamino-3-methyl-6-thien-2-yl-1,2,4-triazin-5-one.

16. Compound as claimed in claim 1 designated 4-amino-3-ethyl-6-thien-2-yl-1,2,4-triazin-5-one.

17. Compound as claimed in claim 1 designated 4-methylamino-3-ethyl-6-thien-2-yl-1,2,4-triazin-5-one.

18. Compound as claimed in claim 1 designated 4-amino-3-ethyl-6-thien-2-yl-1,2,4-triazin-5-one hydrochloride.

19. A herbicidal composition for use in combating weeds comprising, in an agriculturally acceptable carrier, an effective amount of 4-amino-1,2,4-triazin-5-one compound as claimed in claim 1.

20. Method of combating undersired vegetation which method comprises applying to such vegetation or their habitat herbicidally effective amounts of 4-amino-1,2,4-triazin-5-one compounds of the formula

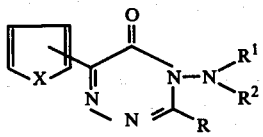

(I), wherein

R is hydrogen, alkyl of up to 6 carbon atoms, alkenyl of up to 6 carbon atoms, cycloalkyl of from 3 to 6 carbon atoms, phenyl, phenylalkyl, wherein the alkyl moiety has up to 2 carbon atoms, substituted phenyl, and substituted phenylalkyl wherein the benzene moiety is substituted with at least one of halogen, hydroxyl alkyl of up to 4 carbon atoms, alkoxy of up to 4 carbon atoms, or haloalkyl of up to 2 carbon atoms and up to 5 halo atoms, $R^1$ is hydrogen or alkyl of up to 6 carbon atoms, $R^2$ is hydrogen, alkyl of up to 6 carbon atoms, haloalkyl of up to 4 carbon atoms and up to 5 halo atoms, phenyl, phenylalkyl of up to 2 carbon atoms in the alkyl moiety, substituted phenyl, and substituted phenylalkyl wherein the benzene ring is substituted with at least one of halogen alkyl of up to 4 carbon atoms, alkoxy of up to carbon atoms or alkylthio of up to 4 carbon atoms, and X is oxygen, sulfur or the NH group or a salt thereof.

21. Method as claimed in claim 20 wherein R. is hydrogen.

22. Method as claimed in claim 20 wherein R is alkyl or alkenyl of up to 6 carbon atoms.

23. Method as claimed in claim 20 wherein R is cycloalkyl of 3 to 6 carbon atoms.

24. Method as claimed in claim 20 wherein R is phenyl, or phenylalkyl of 1 to 2 carbon atoms in the alkyl moiety and wherein the benzene ring may be substituted by halogen, hydroxyl, alkyl or alkoxy of up to 4 carbon atoms or haloalkyl of 1 to 2 carbon atoms and 2 to 5 halogen atoms.

25. Method as claimed in claim 20 wherein $R^1$ is hydrogen.

26. Method as claimed in claim 20 wherein $R^1$ is alkyl of up to 6 carbon atoms.

27. Method as claimed in claim 20 wherein $R^2$ is hydrogen.

28. Method as claimed in claim 20 wherein $R^2$ is alkyl or haloalkyl of up to 4 carbon atoms.

29. Method as claimed in claim 20 wherein $R^2$ is phenyl or phenylalkyl of 1 to 2 carbon atoms in the alkyl moiety wherein the benzene ring may be substituted by halogen or alkyl, alkoxy or alkylthio of up to 4 carbon atoms.

30. Method as claimed in claim 20 wherein X is oxygen.

31. Method as claimed in claim 1 wherein X is sulfur.

32. Method as claimed in claim 1 wherein X is the NH group.

,31

33. Method as claimed in claim 20 wherein said compound is designated 4-amino-3-methyl-6-thien-2-yl-1,2,4-triazin-5-one.

34. Method as claimed in claim 20 wherein said compound is designated 4-methylamino-3-methyl-6-thien-2-yl-1,2,4-triazin-5-one.

35. Method as claimed in claim 20 wherein said compound is designated 4-amino-3-ethyl-6-thien-2-yl-1,2,4-triazin-5-one.

36. Method as claimed in claim 20 wherein said compound is designated 4-methylamino-3-ethyl-6-thien-2-yl-1,2,4-triazin-5-one.

37. Method as claimed in claim 20 wherein said compound is designated 4-amino-3-ethyl-6-thien-2-yl-1,2,4-triazin-5-one hydrochloride.

* * * * *